(12) United States Patent
Passarelli, Jr.

(10) Patent No.: US 6,561,035 B2
(45) Date of Patent: May 13, 2003

(54) ELECTROMAGNETIC ACOUSTIC TRANSDUCER WITH RECESSED COILS

(76) Inventor: Frank Passarelli, Jr., 4634 Tam OShanter Dr., Westlake Village, CA (US) 91362

( * ) Notice: Subject to any disclaimer, the term of this patent is extended or adjusted under 35 U.S.C. 154(b) by 0 days.

(21) Appl. No.: 09/991,147

(22) Filed: Nov. 13, 2001

(65) Prior Publication Data

US 2002/0092353 A1 Jul. 18, 2002

Related U.S. Application Data

(60) Provisional application No. 60/248,991, filed on Nov. 15, 2000.

(51) Int. Cl.[7] .................. G01N 29/24; G01N 29/06; G01N 29/26
(52) U.S. Cl. ........................... 73/643; 73/622
(58) Field of Search .................. 73/643, 622, 623, 73/579, 597, 598, 599, 600

(56) References Cited

U.S. PATENT DOCUMENTS

| | | | | |
|---|---|---|---|---|
| 4,127,035 A | * | 11/1978 | Vasile | 73/629 |
| 4,232,557 A | * | 11/1980 | Vasile | 73/629 |
| 4,471,658 A | * | 9/1984 | Morimoto | 73/643 |
| 4,976,148 A | | 12/1990 | Migliori et al. | 73/579 |
| 5,062,296 A | | 11/1991 | Migliori | 73/579 |
| 5,456,113 A | * | 10/1995 | Kwun et al. | 73/587 |
| 5,581,037 A | * | 12/1996 | Kwun et al. | 73/623 |
| 5,808,202 A | | 9/1998 | Passarelli | 73/643 |
| 5,895,856 A | | 4/1999 | Johnson | 73/643 |
| 6,109,108 A | | 8/2000 | Ohtani et al. | 73/599 |
| 6,119,522 A | | 9/2000 | Johnson | 73/643 |
| 6,164,137 A | | 12/2000 | Hancock | 73/643 |
| 6,170,336 B1 | | 1/2001 | Johnson | 73/643 |

OTHER PUBLICATIONS

Bray, Don E. and Stanley, Roderic K., *Nondestructive Evaluation, A Tool In Design, Manufacturing, and Service*, Revised Edition. CRC Press Boca Raton, New York, London, Tokyo. 1997 pp. 382 and 385.

* cited by examiner

*Primary Examiner*—Daniel S. Larkin
*Assistant Examiner*—Rose M. Miller
(74) *Attorney, Agent, or Firm*—Brooks & Fillbach; Michael Blaine Brooks

(57) ABSTRACT

The disclosed invention mounts transmitting and receiving electrical coils (52, 54) within channels or chambers (48, 50) formed by the notched ends of magnets (24, 28) closest to the metallic structure under test (40) where said magnets (24, 28) are arranged to form annular arrays (20, 22) of an electromagnetic acoustic transducer (EMAT) pair applicable in non-destructive testing. The detection of one or more electromagnetically-induced resonant frequencies at shifted locations indicates the presence of one or more flaws (58, 60) in the metallic structure under test (40). The novel recessed mounting of the coils provided by the channels or chambers (48, 50) substantially reduces the observed electrical cross-talk between coils (52, 54) over the prior art and reduces the likelihood of the coils (52, 54) making contact with the subject metallic structure under test (40) as it is in longitudinal motion relative to the coils (52, 54).

10 Claims, 3 Drawing Sheets

ELECTROMAGNETIC ACOUSTIC TRANSDUCER WITH RECESSED COILS

CROSS-REFERENCE TO RELATED APPLICATION

This application claims the benefit of Provisional Patent Application Ser. No. 60/248,991 filed Nov. 15, 2000, the contents of which are incorporated herein by reference.

BACKGROUND OF THE INVENTION

1. Field of the Invention

The field of this invention relates to electromagnetic acoustic transducers usable with substantially cylindrical objects, and methods for determining resonant frequencies and identifying physical properties, particularly flaws, of the substantially cylindrical objects using electromagnetic acoustic transducers with coils recessed into parallel arrays of magnets arranged in a radial fashion transverse to the longitudinal axis of the cylindrical objects.

2. Description of the Prior Art

Inspections according to and as required by government regulations and industry standards are commonly performed on commercially manufactured products including steel and aluminum pipes and tubing and also including elongated, substantially cylindrical bar stock, such as those used in pressurized applications, and also including elongated, substantially cylindrical bar stock, such as those used in high torque applications, e.g., fastenings. The subjects of these regulations and standards are the qualitative and quantitative standards controlling the properties of materials, such as strength, granularity and the presence and severity of flaws.

Clearly, the presence of certain defects can adversely affect the safety and structural integrity of the finished product. It is therefore preferred that the flawed portions of these metallic stocks and commercially manufactured products be economically identified and removed with the flawed portions of these materials recycled. In addition, the need to correct and improve processes and machinery by identifying flaw-producing causal relationships motivates actions that subject the removed portions to further inspections prior to recycling.

It is well known that in the fabrication and refinement of metallic articles, the foundry process itself, as well as errant machinery and other equipment used in the fabrication and refinement can produce one or more unacceptable flaws in the product articles. Present common practice in accordance with current quality control programs places an entire production run subject to rejection due to flaws in a small, but statistically significant, number of parts. There exists economic motivation to detect such flaws directly and thereby indirectly identify one or more problems with the manufacturing equipment or process. Once identified and corrected, manufacturers may then work to minimize the future generation of flawed metallic structures as well as the magnitude of the rejected stock under test. Varying degrees of economic benefit may be gained by the use of various test techniques in ascertaining the location of a flaw and determining the type of flaw.

Presently, there exist a variety of test techniques available and known to practitioners in the field that manufacturers may implement separately or in combination to determine flaws in metallic structures. Generally, one may dichotomize these as destructive and non-destructive test techniques. In destructive testing, a selected portion of the subject metallic item is destroyed; a portion that could very well be flawless while the remaining unselected portions of the metallic part may contain numerous unacceptable flaws. The extensibility of the results of destructive testing of a portion of the metallic item to the remainder of the item can vary greatly.

The principal advantage of non-destructive testing is that the metallic structure is examined throughout with only the flawed portion being isolated and removed, thereby leaving the unflawed portion for immediate usage. Typically, once a flawed portion in the metallic structure is determined, the testing procedure and/or device employs some means to ascertain the location of that flaw and the metallic structure is marked accordingly. With respect to non-destructive test techniques, there is a wide range of technology available including the use of eddy currents, magnetic flux leakage, x-ray, ultrasound, neutron detraction, and so forth. Where commercially practical non-destructive testing is implemented, one skilled in the art typically places one or more of devices embodying at least one of these non-destructive technologies within the production line so as to ascertain a flawed portion of a particular metallic structure during the normal production of a metallic structure.

Practitioners in the field are generally aware of the use of acoustic resonance techniques in the non-destructive testing of metallic structures. The use of acoustic resonance can offer significant advantages over other prior art types of non-destructive testing technologies. However, acoustic resonance techniques of the prior art have met with limited success due to the difficulty and expense in applying such especially with the use of contact type transducers.

Contact-type transducers, by their mechanical nature, affect the intrinsic resonance of the metallic structure since such transducers, by necessity, come into mechanical contact with the metallic structure. The affect the testing device has on the metallic part under test leads to complex signal and processing schemes to account for the variation in resonance such as taught by U.S. Pat. No. 5,062,296 to Magliori and U.S. Pat. No. 4,9766,148 to Magliori, et al. These inventions employ a ceramic piezoelectric transducer, one that is typically a contact-type of transducer. A non-destructive testing device that does not require contact with the metallic part under test would be preferred so that the metallic structures under test resonate in isolation and thereby forgo the complexities and uncertainties associable with the contact-type signal processing.

Non-destructive testing can be performed by electromagnetic acoustic transducer (EMAT) devices disclosed in U.S. Pat. No. 6,190,108 to Ohtani, et al., U.S. Pat. No. 6,164,137 to Hancock, et al., U.S. Pat. Nos. 5, 895,856, 6,119,522 and 6,170,336 all to Johnson, et al. (collectively referred to as Johnson) and in U.S. Pat. No. 5,808,202 to Passarelli. Ohtani discloses burst wave technique with an apparatus using a sheet coil. Hancock discloses a technique for tubes using dual circumferential acoustic waves produced by a transmitting EMAT and sensed by a pair of receiving EMATs. Johnson and Passarelli disclose EMATs typically in arranged one or more planes of magnets of alternating polarities arrayed in a radial fashion about a substantially annular orifice or pass-through hole and transverse to the longitudinal axis of the substantially cylindrical object under test. Electrical wire is then positioned about each magnet array. Passarelli and Johnson disclose EMATs that can provide flaw detection at various levels within a metallic structure under test. This detection in depth offers significant advantages over Hancock when moving from tubular to substantially solid objects under test.

Passarelli discloses each plane pair, together with transmitting and receiving coils and signal processing, act as the transmitting and receive circuit and provide the fields producing the resonance frequencies in the metallic structures under test. Observations gathered from field trials in both steel and aluminum mills indicate that there is an unacceptable decrease in the distance from the metallic part under test to the transducer coils. That is, the gap distance is decreased for the larger sample sizes of metallic structures of one inch or greater in diameter or maximal transverse dimension, limiting the degree to which one may locate the transmitting and receiving coils in closest practical proximity to one another, as is done for smaller diameter metallic structures such as around one-eighth to three-eights inch in diameter. On the other hand, if the gap distance is practically minimized, the electrical benefit is that the field coupling into the metallic structure is maximized and the cross-talk leaking into an adjacent transducer is minimized.

Under typical milling conditions, a metallic structure such as a pipe or tube moves at around three hundred feet per minute relative to the transducer. In the course of ordinary milling condition, the metallic structure moves laterally, or wobbles, and it is this wobble, in practice, that causes the metallic structure to mechanically contact the transducer. That is, as the gap distance decreases, the metallic structure under test is at great risk of coming into contact with the transducer causing damage to the transducer and posing a hazard to mill operations. Thus, a disadvantage of Passarelli and Johnson is that one cannot both accommodate the larger stock and ensure, under continuous mill conditions, the safe passage of the material structure in conjunction with the transducer, because the gap distance from the metallic part to the transducer coil cannot be practicably decreased within the prior art to acceptable distances.

There is another disadvantage to the aforementioned prior art arrangement in that the geometry of the coil used in conjunction with the transducer has an aspect ratio, thin and wide, that naturally causes the solenoid coil to have substantially field emanating from the coil ends along its Z axis. Increasing coil thickness to improve coil performance by tightening up the field produces marginal improvement. But the major disadvantage is that the magnets must be moved further away in order to accommodate the thicker coil. This is not a satisfactory tradeoff since the magnetic field provided by the magnets decreases as the square of the distance from the metallic structure.

An additional difficulty posed by the prior art EMAT structure is that in order to achieve a minimal level of direct coupled signal from the transmitter coil to the receiver coil, the coil turns count must be reduced to enable the coils to be spaced further apart, thus decreasing the defect size resolution. The path length over which the resonance sound field traverses is longer and therefore increase the material's volume under resonance.

SUMMARY OF THE INVENTION

A non-destructive testing apparatus is disclosed comprised of a pair of EMATs; a first EMAT for the transmission and inducement of acoustic waves intended to establish resonances within the metallic structure under test and a second EMAT for the reception of the induced acoustical resonances. Each EMAT is comprised of an electrical coil mounted within a channel or chamber formed by the notched ends of magnets where said magnets are arranged to form an annular array in a radial fashion transverse to the longitudinal axis of the metallic structure under test. The novel recessed mounting of the coils provided by the channels or chambers substantially reduces the observed electrical cross-talk between coils over the prior art and reduces the likelihood of the coils making contact with the subject metallic structure under test while the metallic structure is in longitudinal motion relative to the coils.

In practice, a particular reference resonant frequency is known or can be calculated for an unflawed metallic structure. The transmitting coil is supplied power which when combined with the force of the magnets will cause the metallic structure to vibrate within a range that is to include a resonant frequency. As the magnetic structure passes relative to the transducers and when a flaw is detected, the resonant frequency is shifted out of the range established for an unflawed metallic structure. This shifted resonant frequency can be above the range or below the range for the unflawed metallic structure. The induced resonant frequency of the metallic structure is sensed by the receiving transducer and then by a voltage/current sensor, such as an AM detector, transmitted via an analog-to-digital converter to a computer. Associated with the transmitting transducer and receiving transducer pair is some form of optional marking device that is capable of marking the metallic structure at the point of the flaw once the resonant frequency of the flaws portion exceeds the unflawed range as determined by the computer.

The subject matter of this invention is constructed so that each array of magnets located in conjunction with each transducer has a channel, or chamber formed therein. Within this channel is located an electrical coil. This placement of the electrical coil is different from prior art where the coil was mounted on the exterior surfaces of the magnets closest to the metallic structure under test. This novel accommodation and placement of the coils within the channel or chamber formed by the magnets of the transmitting transducer and the receiving transducer: (1) permits the transmitting transducer and receiving transducer to be enclosed within a single housing and located in close proximity to the metallic structure being tested and (2) substantially reduces the cross-talk between the transmitting transducer and the receiving transducer.

The advantages of using the construction of the transducers of this invention are as follows: (1) with respect to aspect ratio, the coil aspect ratio can now be altered making the coil thicker and narrower without moving the permanent magnet array farther from the metallic structure (i.e., the same coil winding density, or turns ratio, is maintained and therefore, the coil's inductive properties can better match those of a wider coil design); (2) with respect to tighter acoustic field dispersion, the narrower coil now produces a narrow acoustic field that is generated by the transmitter transducer and the channel within which the coil is mounted can be moved so as to maximize the detection resolution depending upon measurement requirement; (3) with respect to solenoid coil side lobe reduction, the solenoid coil that is mounted within the channel of the magnets significantly reduces cross talk, (i.e., the electromagnetic signal that directly couples from the transmitting transducer into the receiving transducer) and this mounting of the coil within a channel of the magnets effectively provides a shield to reduce this cross-talk by a factor greater than ten from prior art structures such as disclosed in U.S. Pat. No. 5,808,202 to Passarelli; (4) with respect to magnet lift-off distance, the channeled magnet structure of this invention decreases magnet lift-off distance by bringing the edges, or skirts of the magnets, closer to the metallic structure being tested by a factor equal to the coil thickness and thereby strengthens the direct current bias field supplied by the magnets by a factor of square of the distance although the magnets and coil are not inline with each other at these skirts and the additional field provided by the magnets improves transduction efficiency; (5) with respect to coil protection, the soft coil is now recessed into the relatively hard magnet skirt providing added protection from coil impact damage due to possible contact of the coil by the metallic structure under test; and (6) with regards to multi-frequency operation from a single transducer, with coil impedance properties being stabilized, it becomes practical to drive a single transducer at multiple frequency bands, resulting in a single transducer transmit and receive pair capable of inspecting multiple sample cross-sections or depths.

DETAILED DESCRIPTION OF THE PREFERRED EMBODIMENT

Figure 1:
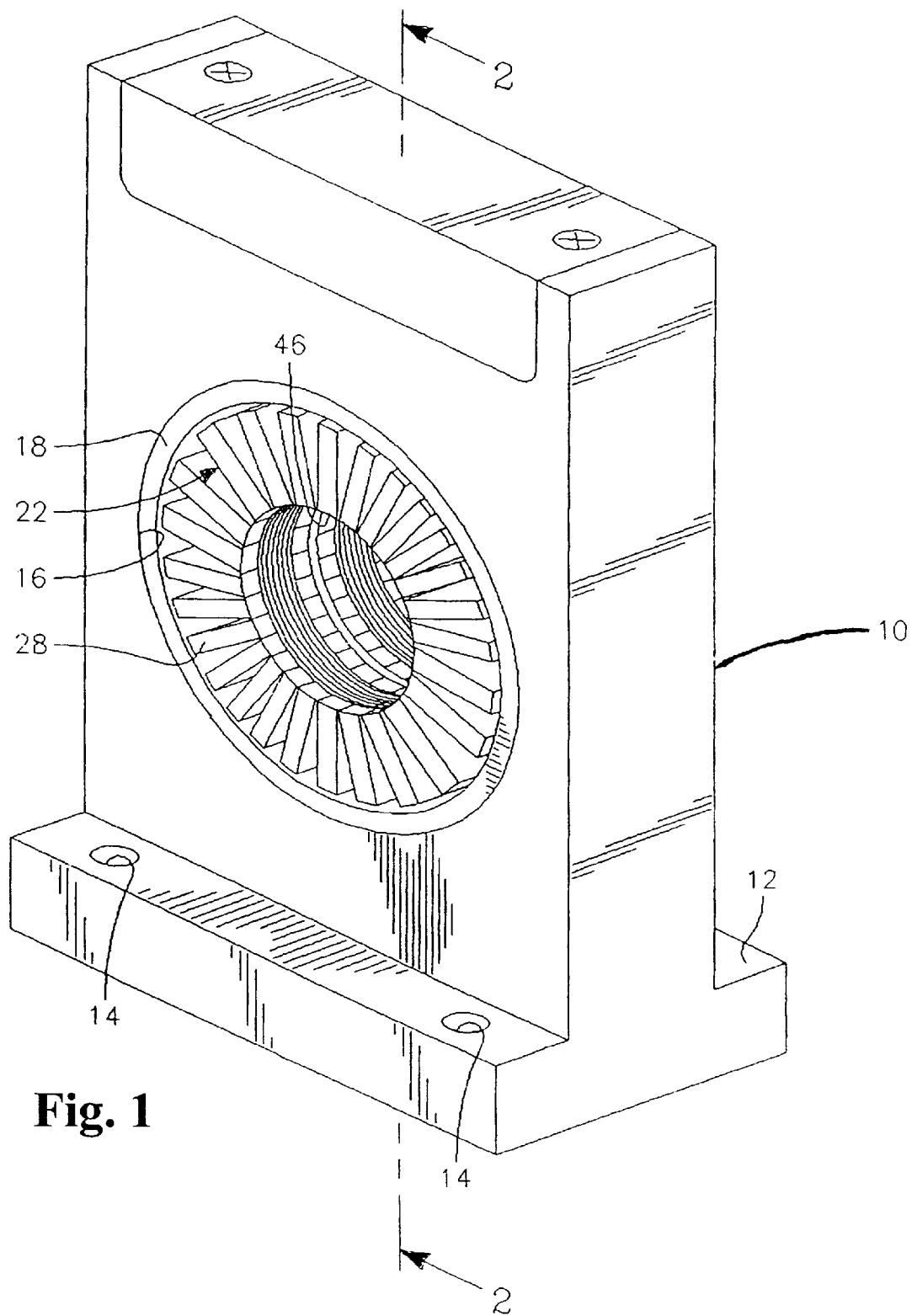
FIG. 1 is an isometric view of the transducer assembly of the present invention which comprises a transmitting transducer and a receiving transducer mounted in conjunction with a single housing.

A novel approach of the present invention has to do with mounting transmitting and receiving electrical coils within channels or chambers formed by notched, grooved or otherwise channeled ends of magnets closest to the metallic structure under test where said magnets are arranged to form annular arrays of an EMAT pair applicable in non-destructive testing. The detection of one or more electromagnetically-induced resonant frequencies at shifted locations indicates the presence of one or more flaws in the metallic structure under test. The use of the EMAT pair permits continuous scanning along the axis of an elongated metallic structure thus giving the flaw detection apparatus of this invention utility in a moving production line. Because the EMAT is intended to not contact the metallic part, distortion is thereby minimized, except for accidental contact, which would be caused by the mechanical impedance mismatch endemic to the contacting method of ultrasonic resonance generation. The use of an EMAT enables a precise segmented range or scan of vibrational frequencies of the metallic structure and its wave mode selectivity minimizes the generation of parasitic acoustic vibrations that may dilute the frequency resolution of the flaw detection system.

The use of an EMAT for the generation and detecting of resonances within metallic structures is radically different from other ultrasonic flaw detection systems. EMATs effectively address the issues of the prior art that have hindered the use of acoustic resonance in non-destructive testing. Using an EMAT for the generation of acoustic resonance provides a signal fidelity advantage of several orders of magnitude over all other known types of ultrasound-based flaw detection apparatuses.

Operation of the system of the present invention takes full advantage of resonance principles. The operator, after selecting and installing the appropriate size of the transducer for the given application, enters the type of material and its shape into the computer. The software in the computer can then calculate the range of frequencies that should be subjected to the metallic structure in order to obtain a resonant frequency for the metallic structure when in an unflawed condition. The software can then control the frequency scans (through the selected range) of the transducer driving electronics. The computer then proceeds with executing via analog electronics a repetitive search for resonation based upon a calculation of at what frequency the metallic structure should resonate. Once resonance is established, the acceptable frequency deviations for both the unflawed condition and the flawed condition for a defect are then established and the sequential frequency scans can then proceed. The range is set for what is determined an unflawed metallic structure that establishes the acceptable limits of an unflawed condition in the metallic structure. This frequency scanning rapidly divides the axis of the metallic structure under test, in the case of tubular goods or the like, into identifiable segments thus providing the ability to locate the position of any anomaly along the longitudinal axis of the tubular goods. The operator or an automated system can then mark the flaw location while the testing process continues. No stopping of the metallic structure is required during the test procedure.

The principles of operation of the flaw detection apparatus of the present invention have specific utility in determining of flaws in cylindrical shapes. However, it is to be understood that the structure of this invention is not intended to be limited to only cylindrical shape geometry. Every metallic structure whose material and structural qualities are considered sound or normal will have vibrational modes that produce resonant frequencies that fall within a typical domain. Resonant behavior outside of that domain represents some range of anomalies that indicate the presence of a qualitative or quantitative defect.

In the specific case of generating vibrational modes in tubes and rods, these types of structures are mathematically treated as uniform cylinders of infinite length. While the structures under test may not fit the exact structure of a uniform cylinder of infinite length, a reasonably accurate prediction can be obtained at those frequencies the structure will resonate. The type of vibrational energy used in conjunction with this invention for flaw detection in rods and tubes comprises axial shear or axial shear-like wave modes. Their wave vector in the azimuthal direction characterizes these axial shear vibrations. The particle motion along the axial direction comprises an integral number of wavelengths around the circumference of the rod or tube. Therefore, the number of magnets incorporated within the transducer determines the number of integral wavelengths around the circumference of the rod or tube.

In order to calculate for the approximate frequency of resonance the following equation is used:

$$F = \frac{BV}{2\pi R}; \quad [1]$$

where F represents the frequency of resonance, B represents a root value of a Bessel function of the second order, V represents the velocity of sound of a horizontal shear wave in the metallic structure and R represents the radius of the metallic structure. Within each EMAT of the present invention, twenty-six different magnets produce thirteen wavelengths. For example, where the metallic structure comprises an elongated length of 6061 aluminum rod having a diameter of 25.4 millimeters and a sound velocity (V) of 3.04 millimeters per microsecond, the first five solutions for B are shown in the following table with the resulting frequency for resonation corresponding to each frequency.

The location as to what portion of the aluminum rod these resonations occurs is also noted.

TABLE

| B | F | Approximate Scan Depth |
|---|---|---|
| 14.928374 | 576.901 KHz | From surface of rod to around .20 inches deep |
| 19.883224 | 768.380 KHz | Below surface at and around .35 inches deep |
| 23.819389 | 920.491 KHz | Below surface at and around .46 inches deep |
| 27.47434 | 1,061.736 KHz | Below surface at and around .54 inches deep |
| 30.987394 | 1,197.497 KHz | Below surface at and around .60 inches deep |

The above table indicates that if the resonant frequency is determined to be around 576 KHz, flaws will be detected in the outer layer of the aluminum rod. At a frequency of about 768 KHz, flaws will be detected below the surface of the aluminum rod around a depth that corresponds to a diameter of 0.65 inches of the rod or tube. At a frequency of 920 KHz, flaws will be detected again below the surface of the rod around the depth of 0.54 inches diameter. Similarly, at a frequency of 1,061 KHz, flaws will be detected below the surface of the rod around 0.46 inches in diameter. Finally, at a frequency of 1,197 KHz, flaws will be detected below the surface of the rod around 0.40 inches in diameter.

It is to be understood that the above-referenced resonant frequencies, in addition to being influenced by the presence of defects, are influenced by variances in alloy composition, temperature, and the diameter of the rod. The effect on resonance caused by the presence of defects presents a significantly different effect on the frequency than other influences. The presence of defects causes the resonant signal to shift position in an abrupt manner. This shift in frequency is due to a decrease in the velocity of the sound being propagated through the rod. The velocity (V) of sound in a solid for a shear wave is determined by the following equation:

$$V = \frac{\sqrt{\mu}}{\rho}; \quad [2]$$

where $\mu$ represents the internal stress and $\rho$ represents the mass density. The internal stress, $\mu$, is substantially affected in the vicinity of the flaw and it is reflected in the resonant frequency.

Referring again to the above table, for the user to discover flaws at the surface level of the metallic structure, it would only be necessary to use an EMAT that is preset to the range of around 576 KHz. However, the EMATs of the present invention provide for the simultaneously determination of flaws in the metallic structure at deeper depths. That is, the EMATs can additionally operate in the range of 768 KHz to detect flaws at and around 0.35 inches below the surface of the metallic structure, in the range of 920 KHz to detect flaws at and around 0.46 inches below the surface of the metallic structure, and other higher frequency ranges to provide the user with flaw detection data substantially through the entire metallic structure.

Figure 2:
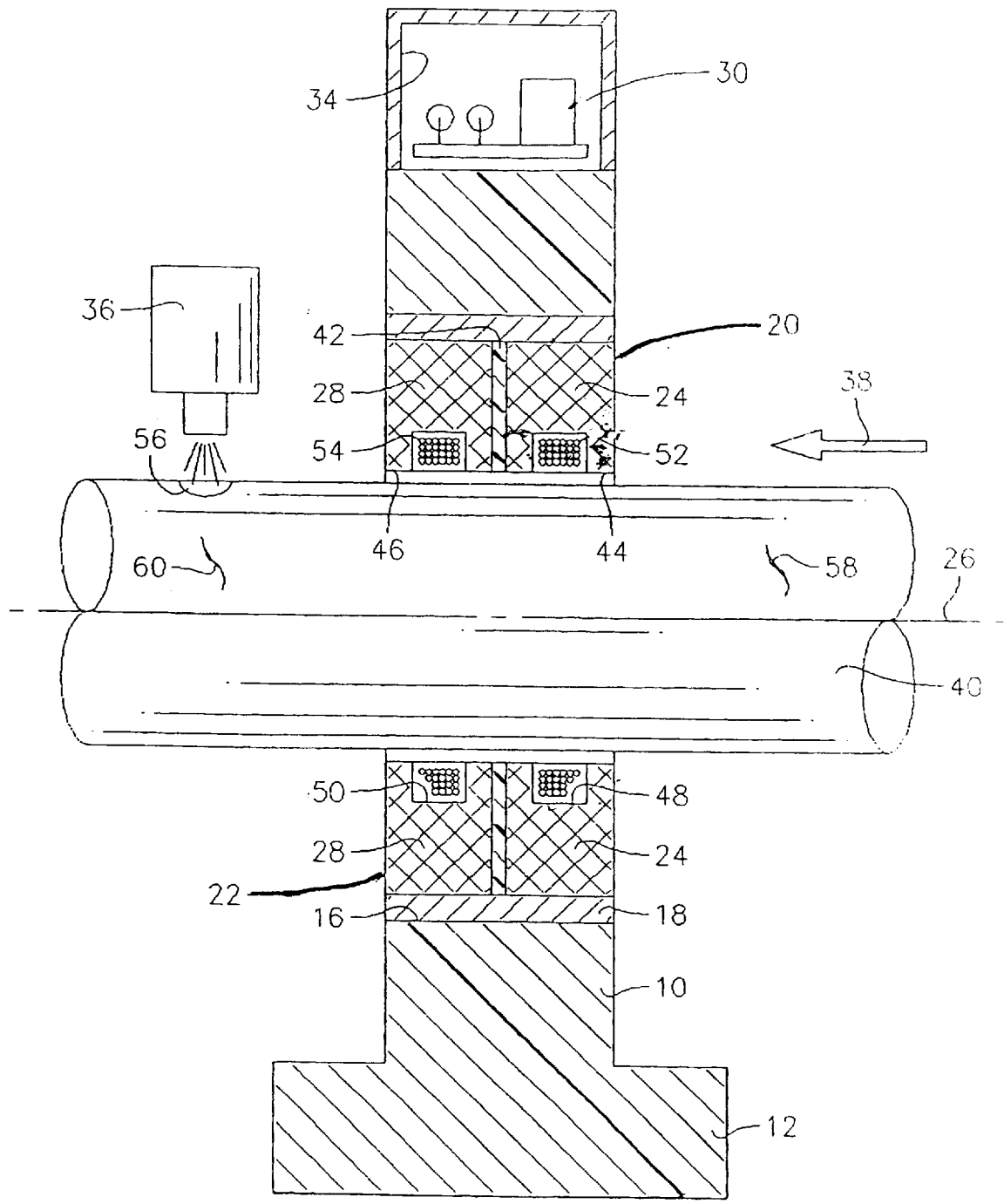
FIG. 2 is a transverse cross-sectional view through the transducer assembly of FIG. 1 taken along 2—2 of FIG. 1.

Referring particularly to the drawings, FIG. 1 illustrates a housing 10 that houses the flaw detection apparatus of this invention. FIG. 2 illustrates the housing from the perspective of a transverse cross-sectional view through the transducer assembly of FIG. 1 taken along 2—2 of FIG. 1. The housing 10 includes a base 12 mountable to on an exterior structure by using bolt-type fasteners working in conjunction with holes 14. The housing 10 includes a pass-through opening 16. Mounted within the pass-through opening 16, in a snug fitting manner, is a steel sleeve 18. Mounted within the confines of the steel sleeve 18 are a first series of magnets 20 and a second series of magnets 22. It is understood that the term magnet refers to permanent magnets and to ferrite materials and otherwise magentizable materials applied separately or in combinations to form an article. The first series of magnets 20 includes a plurality of first series magnets 24 and the second series magnets 22 includes a plurality of second series magnets 28. In the preferred embodiment, there are twenty-six in number of first series magnets 24 each of which assumes a radial and substantially evenly spaced position relative to a longitudinal center axis 26. The number of first series magnets 24 can vary with specific applications. The longitudinal center axis 26 passes through the center of the pass-through opening 16. The first series magnets 24 complete an entire circular pattern, or array, and each of the first series magnets 24 are substantially of the same size and composition. Every other magnet in the first series of magnets 20 are arranged so that the north and south poles of a particular first series magnet 24 are reversed relative to a immediately adjacent magnet of the same series. That is, the first series magnets 24 are in an alternating polarity (north-south) array. The second series magnets 28 of the preferred embodiment are also twenty-six in number. As with the first series magnets 24, the number of second series magnets 28 can vary with specific applications. The second series of magnets 22 are located in juxtaposition to the first series of magnets 20, in arrays of substantially parallel planes. The second series magnets 28 are not axially aligned with the first series magnets 24 but are instead angularly displaced, that is axially rotated from alignment, a few degrees from one array to the other. In practice for two twenty-six magnet arrays, this angular displacement amounts to about 6.92 degrees as each of the first series magnets 24, when comprised of twenty-six in number, is located about 13.846 degrees apart from one another, the same displacement also being true for second series magnets 28.

The first series of magnets 20 and the second series of magnets 22 connect electrically to appropriate electronic components 30 which are contained with a compartment 34 of the housing 10. These electronic components 30 connect appropriately to necessary operating structures, such as a computer (not shown). The computer drives a marking device 36, such as a spray painting mechanism, mounted close to, but just down stream of, the housing 10 relative to the path of travel represented by the directional arrow 38 of the metallic tubular structure 40. Under typical milling conditions, the metallic tubular structure 40 passes through the pass-through opening 16 at about three hundred feet per minute.

Between the first series of magnets 20 and the second series of magnets 22, there is a dielectric spacer 42. The function of the spacer 42 is to fixedly establish the spacing between the first series of magnets 20 and the second series of magnets 22.

The inside surfaces of the first series magnets 24 form a circular-shaped pass-through opening 44. Similarly, the inside surfaces of the second series magnets 28 form a cylindrically shaped pass-through opening 46. The inside surfaces of the first series magnets 24 each include a recess so there is formed a substantially continuous first annular channel or chamber 48. For purposes of creating the recess or annular channel or chamber for the coil, it is understood that the term notch is used to represent am modification to each magnet whereby material is added to or removed from each magnet. A similar substantially continuous second annular channel or chamber 50 is formed within the inside surface of the second series magnets 28. Mounted within the first annular chamber 48 is a transmitting coil 52. Mounted within the second annular channel or chamber 50 is a receiving coil 54. The transmitting coil 52 and the receiving coil 54 each comprise a coil spool on which is wound wire. Each of the wires of each coil 52 and 54 terminates in a pair of leads (not shown). These leads (not shown) connect to the electronics 30. The wires of the coils 52 and 54 typically comprise copper wire of a very small diameter. The size of the wire is variable with the particular size being selected solely in accordance to individual desires and specific applications. The transmitting coil 52 and first series magnets 24 comprise the transmitting transducer, and the receiving coil 54 and second series magnets 28 comprise the receiving transducer.

Given the parameters for detection of flaws, any computer programmer sufficiently skilled in basic signal processing algorithms and real-time programming could design an appropriate computer program to be executed by the computer the purpose of detecting flaws, such as first sample flaw 58 and second sample flaw 60 within the metallic structure 40 using the herein disclosed EMATs. The computer transmits an output signal to a programmable signal generator (not shown). The purpose of the signal generator is to generate a sweeping sine wave upon command from the computer. The signal generator transmits its output to an amplifier (not shown). The amplifier transmits the amplified signal to the transmitting transducer comprised of the first series of magnets 20 and the transmitting coil 52. For example, a sweeping or scanning of the signal between 586 KHz and 588 KHz occurs that results in the production of sound flawed frequency spike when a flaw is present. The receiving transducer, comprised of the second series of magnets 22 and the receiving coil 54, detects the sound flawed frequency spike. The receiving coil 54 supplies the detected signal to an amplifier (not shown). From the amplifier, the signal is subject to phase and/or amplitude demodulation (i.e., an AM detector). For example, a diode rectifier (not shown) converts the signal from a sine wave to a DC voltage. The diode provides an output signal to an analog-to-digital converter (ADC) (not shown) that in turn transmits the signal to the computer. In addition, a counter timer (not shown) receives the output of the signal generator. The counter timer circuit synchronizes the activity of the signal generator and the ADC by keeping an accurate count of the number of cycles of each frequency step and recording precisely where and when each step occurs in the scan. If the electromagnetic acoustic transducer-based apparatus of the present invention detects a surface flaw, such as second sample flaw 60, the spiked, or otherwise peaking, area of the frequency will shift with this shift being outside an unflawed frequency area, such as 587.2 KHz. The computer will then document that a detected flaw and will appropriately cause the marking device 36 to be activated to apply a quantity of paint 56 onto the metallic structure 40 in alignment with the flaw 60. In the preferred embodiment, the region of the application of the paint 56 corresponds substantially with the location of the detected flaw in the metallic structure 40. By this marking, the detected flaw becomes apparent to the manufacturer manufacturing the metallic structure 40. That is, the present invention alerts the manufacturer through the marking of the metallic structure 40 with the paint 56 and thereafter, the manufacturer may choose to avoid immediate use of the flawed area. The same detection and marking procedure occurs for subsequent flaws as they present themselves as shifted resonant frequencies.

Figure 3A:
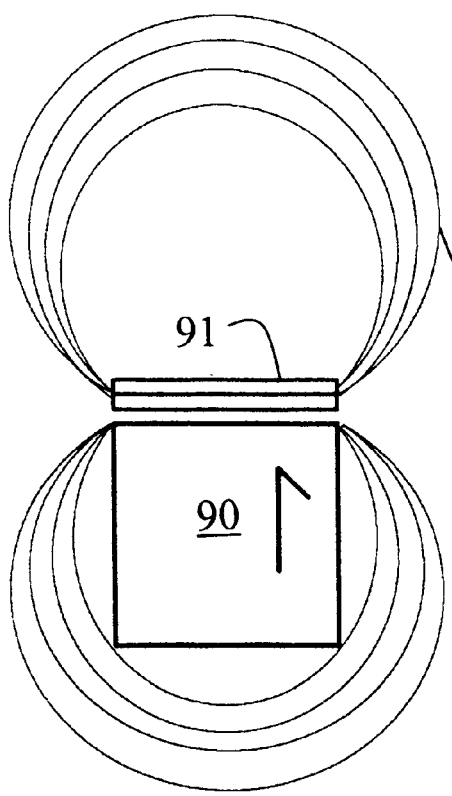
FIG. 3 illustrates the improved field characteristics of the present recessed coil, FIG. 3B as compared with the prior art, FIG. 3A.
Figure 3B:
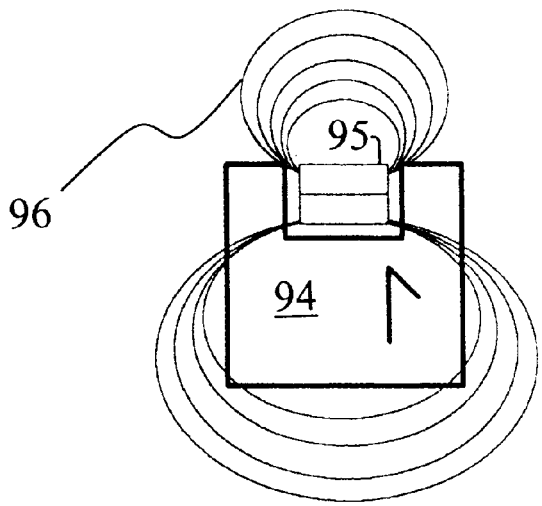

FIG. 3 illustrates, in a transverse view, the solenoid coil side lobe reduction from the side lobes of the prior art 93 in FIG. 3A to the side lobes of the present invention 96 in FIG. 3B. The prior art as disclosed by Passarelli in U.S. Pat. No. 5,808,202 and by Johnson in U.S. Pat. No. 5,895,856 mounts the coil 91 on top of each magnet 90, that is, on the edge of the magnet closest to the metallic structure under test (not shown). As explained above, this mounting of the coil 95 within a channel formed by the notch of each magnet 94 effectively provides a shield for the mounted coil that significantly reduces coil-to-coil cross-talk (e.g., a cross-talk reduction factor greater than ten from prior art structures) by reducing the side lobes 96.

Although the description above contains many specifications, one should not construe these specifications as limiting the scope of the invention but as merely providing illustrations of some of the presently preferred embodiments of this invention. For example, the recessed channel can be of various depths, widths and shapes, the pass-though opening can be of increased or decreased diameter, the number of magnets can be increased or decreased depending on the electromagnetic nature of the substantially cylindrical metallic stock under test whose circumference can have shapes other than circular, such as hexagonal and octagonal.

While this invention is described above in conjunction with specific embodiments thereof, it is evident that many alternatives, modification, and variations will be apparent to those skilled in the art. Accordingly, the intent of the preceding description is to embrace all such alternatives, modifications and variations as fall within the spirit and scope of the appended claims and their legal equivalents.

I claim:

1. An apparatus for nondestructive testing of metallic structures comprising:
   (A) a housing having a circular opening surrounding an exterior circumferential wall of a substantially cylindrical metallic object; said substantially cylindrical metallic object translatable, along its longitudinal axis, through the housing; and
   (B) a first electromagnetic acoustic transducer comprising:
      (1) a first plurality of substantially similar permanent magnets mounted in the housing and arranged in a first array and positioned substantially in planar radial fashion, about a first radial center, around the circular opening at substantially equal intervals with ends of adjacent magnets possessing opposite polarity; said first array positioned transverse to, and with the first radial center substantially colinear with, the longitudinal axis of said substantially cylindrical metallic object; each of said first plurality of substantially similar permanent magnets comprising:
         (a) a first end adjacent to the circular opening and
         (b) a second end substantially perpendicular to and spaced from the circumferential wall wherein the second end is notched in the plane substantially colinear with the longitudinal axis of the substantially cylindrical metallic object; and
      (2) a first electrically conductive wire coil mounted in the housing and positioned within an annular channel formed by the notched second ends of the first plurality of substantially similar permanent magnets.

2. An apparatus for nondestructive testing of metallic structures as claimed in claim 1 further comprising a second electromagnetic acoustic transducer comprising:

(A) a second plurality of permanent magnets, substantially similar to the first plurality of substantially similar permanent magnets, mounted in the housing and arranged in a second array and positioned substantially in planar radial fashion, about a second radial center, around the circular opening at substantially equal intervals with ends of adjacent magnets possessing opposite polarity; the second array being substantially parallel and proximate to the first array; said second array plurality positioned transverse to, and with the second radial center substantially colinear with, the longitudinal axis of the substantially cylindrical metallic object, each of said second plurality of magnets comprising:

(1) a first end adjacent the circular opening and (2) a second end substantially perpendicular to and spaced from the circumferential wall wherein the second end is notched in the plane substantially colinear with the longitudinal axis of the substantially cylindrical metallic object; and (B) a second electrically conductive wire coil mounted in the housing and positioned within an annular channel formed by the notched second ends of the second plurality of permanent magnets.

3. An apparatus for nondestructive testing of metallic structures as claimed in claim 2 wherein the first array is rotationally offset in alignment relative to the second array.

4. An apparatus for nondestructive testing of metallic structures as claimed in claim 3 wherein spacing of each of the second end of the magnets is substantially consistent permitting the longitudinal travel of the substantially cylindrical metallic object without mechanically contacting the apparatus.

5. An apparatus for nondestructive testing of metallic structures as claimed in claim 4 wherein the first array and the second array are each comprised of twenty-six magnets.

6. An apparatus for nondestructive testing of metallic structures as claimed in claim 5 further comprising (A) a signal generator means coupled to the first electrically conductive wire coil;

(B) a signal detector means coupled to the second electrically conductive wire coil;

whereby the signal generator means applies an electrical excitation signal to the first electrically conductive wire coil mounted in the channel of the first array, and the signal detector means senses the electrical response signal in the second electrically conductive wire coil mounted in the channel of the second array.

7. An apparatus for nondestructive testing of metallic structures as claimed in claim 1 wherein an electrical excitation signal applied to the first electrically conductive wire coil induces vibrations in the substantially cylindrical metallic object.

8. An apparatus for nondestructive testing of metallic structures as claimed in claim 2 wherein acoustical vibrations in the substantially cylindrical metallic object electrically excite the second electrically conductive wire coil.

9. An apparatus for nondestructive testing of metallic structures as claimed in claim 2 wherein the first electromagnetic acoustic transducer is separated from the second electromagnetic acoustic transducer by a dielectric spacer.

10. An electromagnetic acoustic transducer comprising:

(A) a plurality of magnets mounted in a housing and arranged in an array and positioned substantially in a planar radial fashion, about a radial center, at substantially equal intervals around a circular opening of the housing with ends of adjacent magnets possessing opposite polarity; said circular opening providing a pass-through for a substantially cylindrical metallic object; said array positioned transverse to, and with the radial center substantially colinear with, a longitudinal axis of the substantially cylindrical metallic object, each of said plurality of magnets comprising:

(1) a first end adjacent to the circular opening and (2) a second end substantially perpendicular to and spaced from the circumferential wall of the substantially cylindrical metallic object wherein the second end is notched in the plane substantially collinear with the longitudinal axis of the substantially cylindrical metallic object; and (B) an electrically conductive wire coil mounted in the housing and positioned within an annular channel formed by the notched second ends of the plurality of magnets.

* * * * *